US010076599B2

(12) United States Patent
Eyrard et al.

(10) Patent No.: US 10,076,599 B2
(45) Date of Patent: *Sep. 18, 2018

(54) DRY PERITONEAL DIALYSIS CONCENTRATE SYSTEM

(71) Applicant: Fresenius Medical Care Deutschland GmbH, Bad Homburg (DE)

(72) Inventors: Thierry Eyrard, Lyons (FR); Philippe Laffay, Sainte Foy les Lyon (FR); Benoit Luaire, Pontcharra sur Turdine (FR)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 366 days.

This patent is subject to a terminal disclaimer.

(21) Appl. No.: 15/091,298

(22) Filed: Apr. 5, 2016

(65) Prior Publication Data

US 2016/0213832 A1 Jul. 28, 2016

Related U.S. Application Data

(63) Continuation of application No. 13/020,254, filed on Feb. 3, 2011.

(51) Int. Cl.
*A61M 1/28* (2006.01)
*A61M 1/16* (2006.01)

(52) U.S. Cl.
CPC ............ *A61M 1/287* (2013.01); *A61M 1/167* (2014.02); *A61M 1/1656* (2013.01); *A61M 1/1666* (2014.02); *A61M 1/1668* (2014.02); *Y10T 137/0318* (2015.04)

(58) Field of Classification Search
CPC .. A61J 1/10; A61J 1/14; A61J 2001/14; A61J 1/1443; A61J 1/1475; A61J 1/2089; A61J 1/2093
See application file for complete search history.

(56) References Cited

U.S. PATENT DOCUMENTS

| 3,685,717 A | 8/1972 | Seiferth et al. |
| 4,386,634 A | 6/1983 | Stasz et al. |
| 5,925,011 A | 7/1999 | Faict et al. |
| 5,944,709 A | 8/1999 | Barney et al. |

(Continued)

FOREIGN PATENT DOCUMENTS

| AU | 570100 | 9/1985 |
| DE | 19825158 | 4/1994 |

(Continued)

OTHER PUBLICATIONS

Tenckhoff et al., "A Simplified Automatic Peritoneal Dialysis System," vol. XVIII Trans. Amer. Soc. Artif. Int. Organs, 1972, pp. 436-439.

*Primary Examiner* — Tatyana Zalukaeva
*Assistant Examiner* — Kai Weng
(74) *Attorney, Agent, or Firm* — Fish & Richardson P.C.

(57) ABSTRACT

A dry peritoneal dialysis (PD) concentrate system may be used in connection with a PD cycler. The dry PD concentrate system includes a concentrate container with at least two concentrate compartments, and at least one of the compartments contains a dry PD concentrate component. At least one of the concentrate compartments has a medical fluid outlet, and at least one of the concentrate compartments has a diluent inlet.

22 Claims, 10 Drawing Sheets

(56) References Cited

U.S. PATENT DOCUMENTS

| | | | |
|---|---|---|---|
| 6,254,567 B1 | 7/2001 | Treu et al. | |
| 6,274,103 B1 | 8/2001 | Taylor | |
| 6,444,174 B1 | 9/2002 | Lascombes | |
| 6,758,975 B2 | 7/2004 | Peabody et al. | |
| 7,544,300 B2 | 6/2009 | Brugger et al. | |
| 7,544,301 B2 | 6/2009 | Shah et al. | |
| 7,892,423 B2 | 2/2011 | Rohde et al. | |
| 8,469,331 B2 | 6/2013 | Burbank et al. | |
| 8,524,086 B2 | 9/2013 | Peterson et al. | |
| 8,545,428 B2 | 10/2013 | Burbank et al. | |
| 8,801,922 B2 | 8/2014 | Wrazel et al. | |
| 9,138,380 B2 | 9/2015 | Jansson et al. | |
| 9,155,824 B2 | 10/2015 | Eyrard et al. | |
| 9,161,980 B2 | 10/2015 | Ernebrant et al. | |
| 2005/0186183 A1 | 8/2005 | DeAngelo et al. | |
| 2006/0093765 A1* | 5/2006 | Mueller | B29C 65/76 428/35.2 |
| 2006/0226080 A1 | 10/2006 | Degreve et al. | |
| 2008/0234654 A1 | 9/2008 | McCarthy et al. | |
| 2010/0051552 A1 | 3/2010 | Rohde et al. | |
| 2010/0069817 A1* | 3/2010 | Falkvall | A61J 1/2093 604/6.11 |
| 2010/0078092 A1 | 4/2010 | Weilhoefer et al. | |
| 2010/0318058 A1* | 12/2010 | Schroder | A61J 1/2093 604/410 |
| 2011/0189048 A1 | 8/2011 | Curtis et al. | |
| 2012/0095392 A1 | 4/2012 | Jensen et al. | |

FOREIGN PATENT DOCUMENTS

| | | |
|---|---|---|
| DE | 19510759 | 10/1996 |
| DE | 102007009269 | 5/2008 |
| DE | 102009058445 | 6/2011 |
| DE | 102010014785 | 10/2011 |
| EP | 1120099 | 8/2001 |
| WO | WO2007016615 A1 | 2/2007 |
| WO | WO 2010/006146 | 1/2010 |
| WO | WO 2010/121972 | 10/2010 |

* cited by examiner

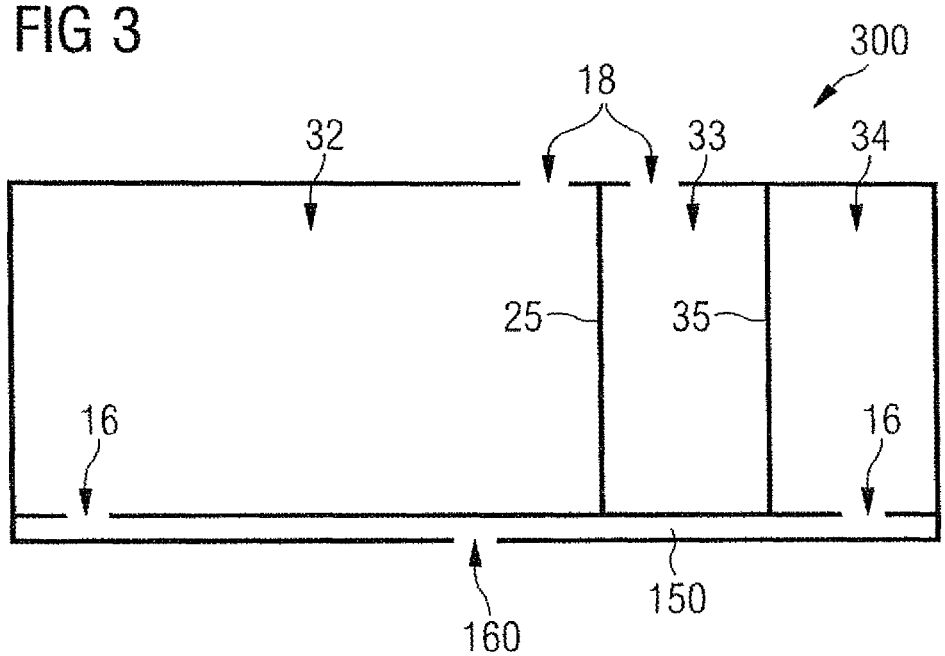
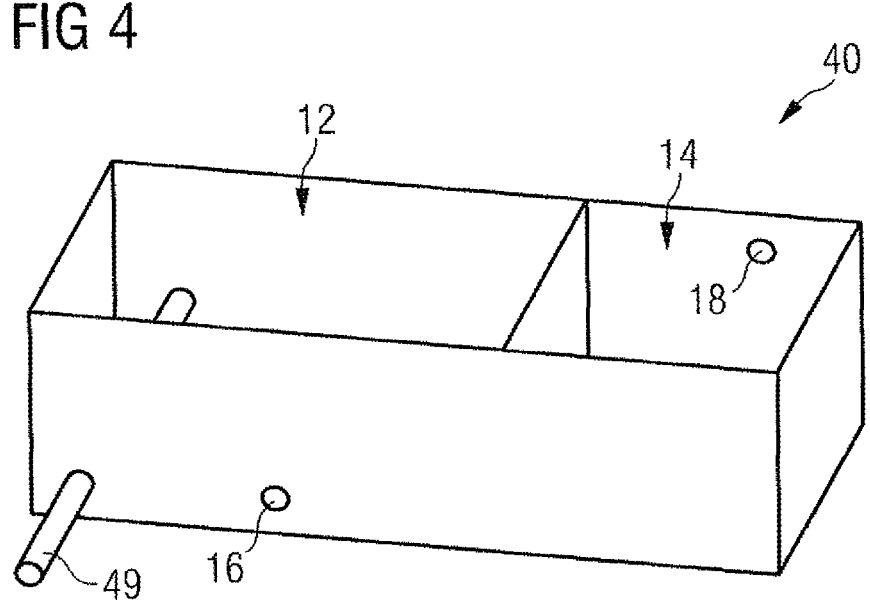

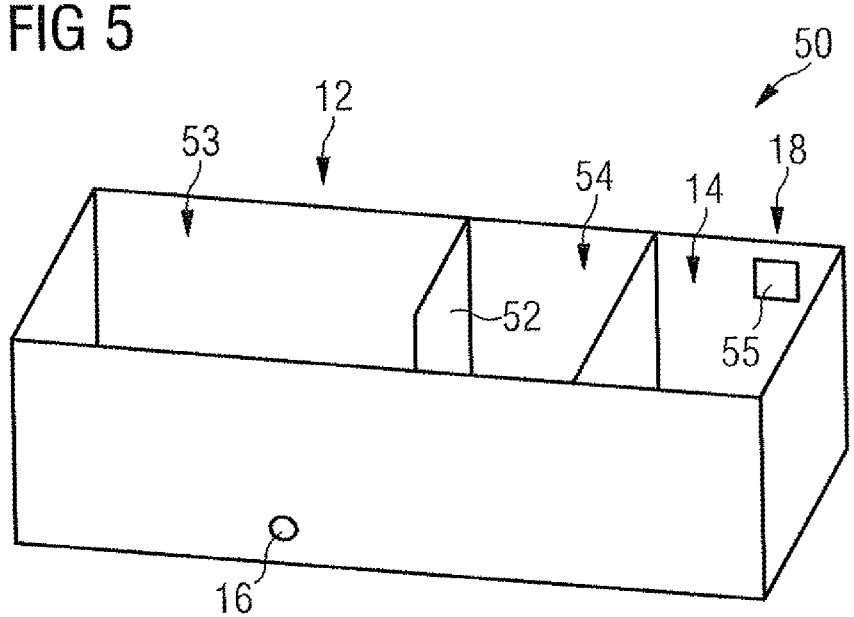
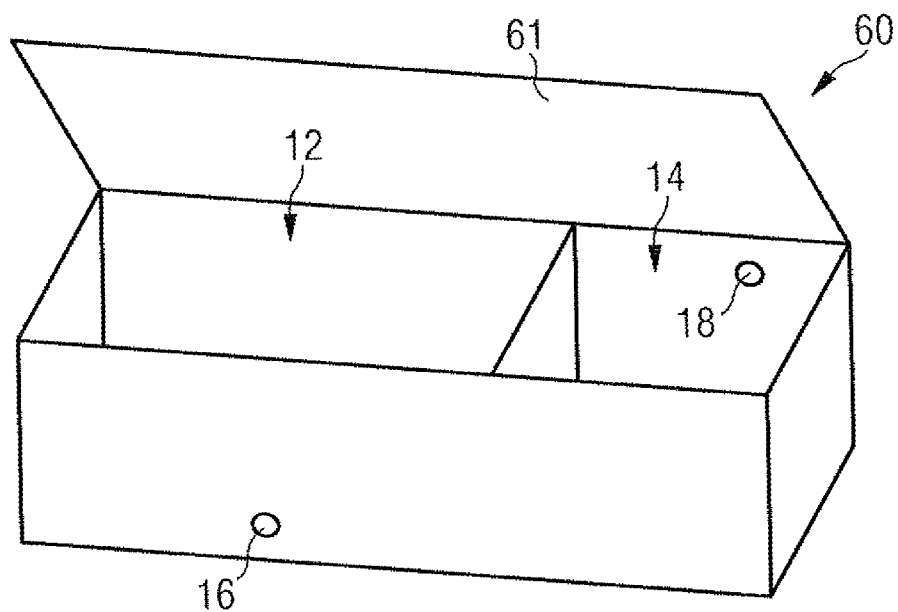

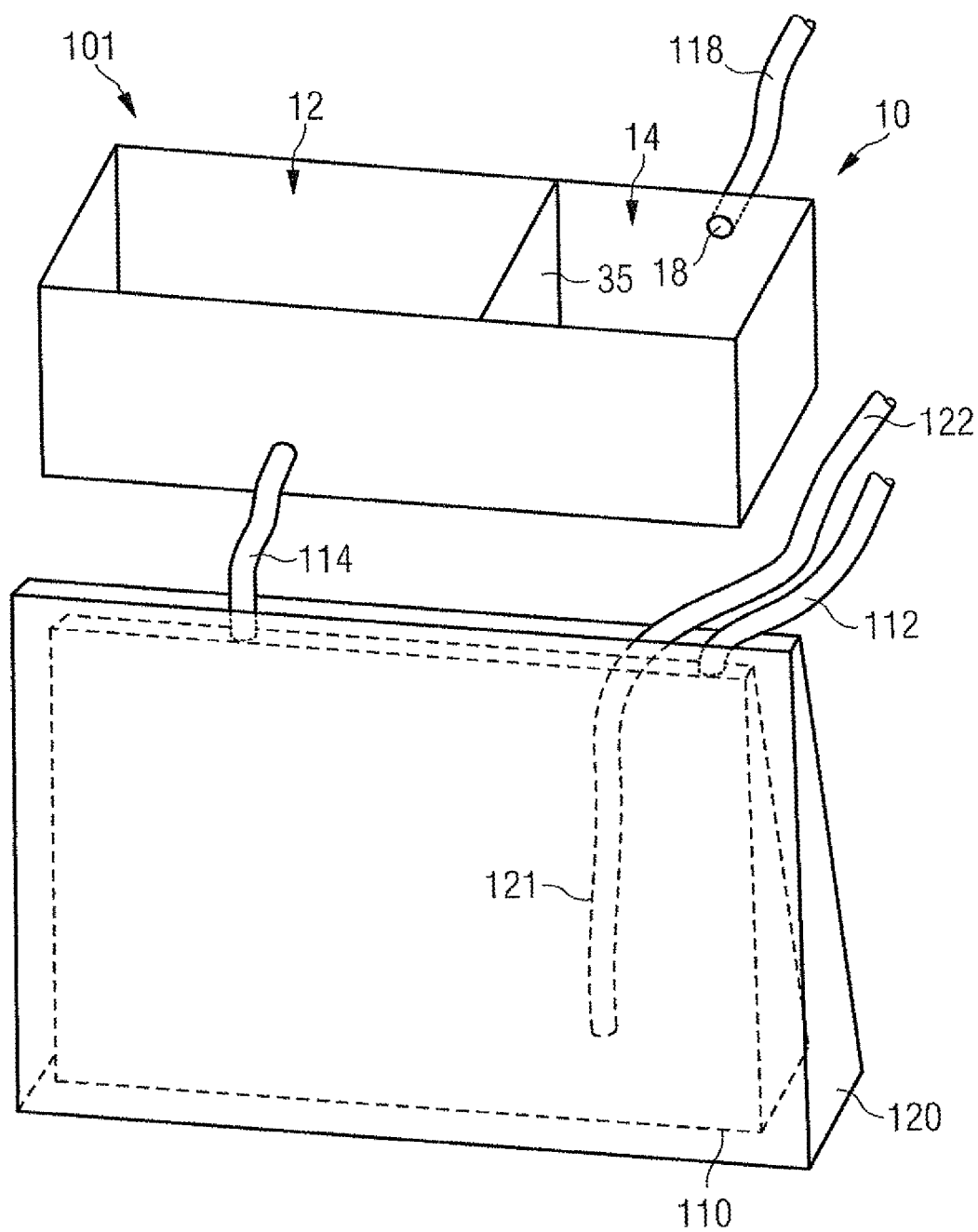

DRY PERITONEAL DIALYSIS CONCENTRATE SYSTEM

RELATED APPLICATIONS

This application is a continuation of U.S. Ser. No. 13/020,254, filed Feb. 3, 2011 (pending), which is incorporated herein by reference.

TECHNICAL FIELD

The present invention is directed to a concentrate container for preparing a medical fluid, to a system for preparing a medical fluid, to a fluid container system, to a kit of parts for preparing a medical fluid, to a use of a system for preparing a medical fluid, and to a method for preparing a medical fluid. In particular, the concentrate container for preparing a medical fluid, the system for preparing a medical fluid, the fluid container system, the kit of parts for preparing a medical fluid, and the method for preparing a medical fluid may be used in dialysis, e.g. acute dialysis, or in hemodiafiltration.

BACKGROUND

Typically, patients with chronic renal failure receive medical treatment three to four times a week either in a dialysis clinic or at home. During hemodialysis, a dialysis machine pumps blood from a vascular access in the patient into a dialyzer. The dialyzer filters metabolic waste products and removes excess water from the blood. These waste products are then flushed out with dialysis solution and the filtered blood is returned to the patient's body. During hemodiafiltration, the machine removes more water from the blood than during hemodialysis. The additional liquid is continually replaced with an ultra-pure electrolyte solution. Thus, the machine exchanges a high volume of fluid during treatment and removes the liquid together with metabolic toxins from the blood.

In peritoneal dialysis, the peritoneum of the patient acts as the filter for cleaning the blood. The peritoneum has characteristics similar to those of the dialyzer: pores in the membrane allow passage of certain substances while retaining others. A catheter is used to introduce dialysis solution into the abdominal cavity. The blood-rich peritoneum is surrounded by the dialysis solution and metabolic toxins flow from the blood through pores in the peritoneum into the dialysis solution. Further, glucose in the dialysis solution pulls excess water out of the body. The solution containing the toxins and excess water is removed through the catheter and replaced with fresh solution. In Continuous Ambulant Peritoneal Dialysis (CAPD), patients change the dialysis solution with the help of bag systems four to five times a day. In Automatic Peritoneal Dialysis (APD), a dialysis machine (cycler) takes over the exchange of fluid, making overnight treatment possible.

Typically, dialysis systems for patients with chronic renal failure are provided with an individual system, in order to supply "reverse osmosis" water (RO water), fresh dialysis solution or concentrate for dialysis solution to the dialysis machine. However, such systems are not practicable for intensive care in hospitals, since in intensive care dialysis machines are used in irregular time intervals and at varying places. Therefore, previous developments aimed at providing dialysis machines with a huge reservoir of dialysis solution, such that the dialysis machines can be used location-independently at any time. Such reservoirs may be provided with an internal container, in order to accommodate dialysis solution. Preferably, the internal container is a bag or pouch having a high volume and which can be disposed after dialysis treatment. If disposables are used, a time consuming disinfection of the reservoir can be omitted.

It is known to use bags for storing a high volume of dialysis solution. Previously, it was necessary to produce the dialysate contained in the bag in a separate device and to transfer the dialysate produced into the bag for storing.

DE 10 2009 058 445 describes a bag for preparing and providing a dialysate batch having a high volume, the bag including concentrate compartments.

AU 570100 B2, DE 195 10 759 A1, U.S. Pat. No. 4,386,634 A and DE 198 25 158 C1 disclose examples, in which a high volume of dialysate is provided in a storage container. The dialysate is contained in a bag having a high volume, which is supported by the storage container.

In DE 10 2007 009 269 A1 a glass tank is provided, in which the dialysate is stored.

EP 1 120 099 B1 describes a cartridge for accommodating concentrates, the cartridge having sub-compartments. The concentrates are dissolved by RO water.

DE 10 2010 014 785 is directed to a plastic film which can be used for the production of a bag having a high capacity for accommodating a dialysate.

Accordingly, it would be desirable to provide a device and a method for preparing a medical fluid.

SUMMARY

In one embodiment, a concentrate container for preparing a medical fluid is provided, preferably for preparing a dialysis solution, the concentrate container including at least two concentrate compartments, wherein at least one of the concentrate compartments has a medical fluid outlet, and at least one of the concentrate compartments has a diluent inlet.

In another embodiment, a fluid container system for preparing a medical fluid is provided, preferably for preparing a dialysis solution, including a fluid container for collecting a prepared medical fluid, the fluid container having a medical fluid drainage line, and another fluid container for collecting a consumed medical fluid, the fluid container being insertable into the another fluid container.

A further embodiment is directed to a kit of parts for preparing a medical fluid, including at least two elements chosen from a concentrate container according to above one embodiment, a fluid container, a fluid container system according to above another embodiment, and a transport means adapted to support and/or to include at least one of the concentrate container, the fluid container, and the fluid container system.

According to a further embodiment, a system for preparing a medical fluid, preferably for preparing a dialysis solution, is provided, the system including a concentrate container according to above one embodiment, a fluid container fluidly connected to a medical fluid removal line, at least one fluid transfer line fluidly connecting the at least one medical fluid outlet of the concentrate container and the fluid container.

According to a yet further embodiment, the concentrate container, the fluid container system, the kit of parts and/or the system for preparing a medical fluid of above embodiments are used in dialysis, acute dialysis, hemodialysis, hemodiafiltration, peritoneal dialysis, or for preparing a dialysis solution.

In another embodiment, a method for preparing a medical fluid, preferably for preparing a medical fluid in a system according to above one embodiment, the method includes providing a concentrate container including at least one concentrate compartment, wherein a first compartment of the concentrate compartments contains a first concentrate; feeding a diluent into the first compartment; rinsing the first compartment by the diluent and diluting the concentrate; and transferring the diluted first concentrate into a fluid container.

BRIEF DESCRIPTION OF THE DRAWINGS

Some of the above mentioned embodiments will be described in more detail in the following description of typical embodiments with reference to the following drawings in which:

FIG. 3 schematically illustrates a concentrate container according to an embodiment of the invention;

FIG. 4 schematically illustrates a concentrate container according to an embodiment of the invention;

FIG. 5 schematically illustrates a concentrate container according to an embodiment of the invention;

FIG. 6 schematically illustrates a concentrate container according to an embodiment of the invention;

FIG. 8 schematically illustrates a system for preparing a medical fluid, according to an embodiment of the invention;

DETAILED DESCRIPTION OF VARIOUS EMBODIMENTS

Within the following description of the drawings, the same reference numbers refer to the same components. Generally, only the differences with respect to the individual embodiments are described. In the following description, embodiments of the invention are described referring to a preparation of a dialysis solution, also referred to herein as dialysate, without limiting the scope of the invention. Other medical fluids may be prepared using embodiments described herein. Further, the terms "concentrate compartment" and "compartment" are used synonymously. Moreover, in embodiments, a concentrate component may also be referred to as a concentrate.

The term "diluent" refers to fluids by which concentrates, e.g. dry concentrates, can be diluted, dissolved or suspended. Some embodiments described herein refer to a solvent as a "diluent", but are not restricted thereto. Further, embodiments described herein using the term "diluent" encompass examples in which in at least two of the concentrate compartments different diluents or solvents can be or are introduced. In addition, in some embodiments, the term "diluting" or "dilution" may encompass dissolution and/or suspension processes.

Figure 1A:
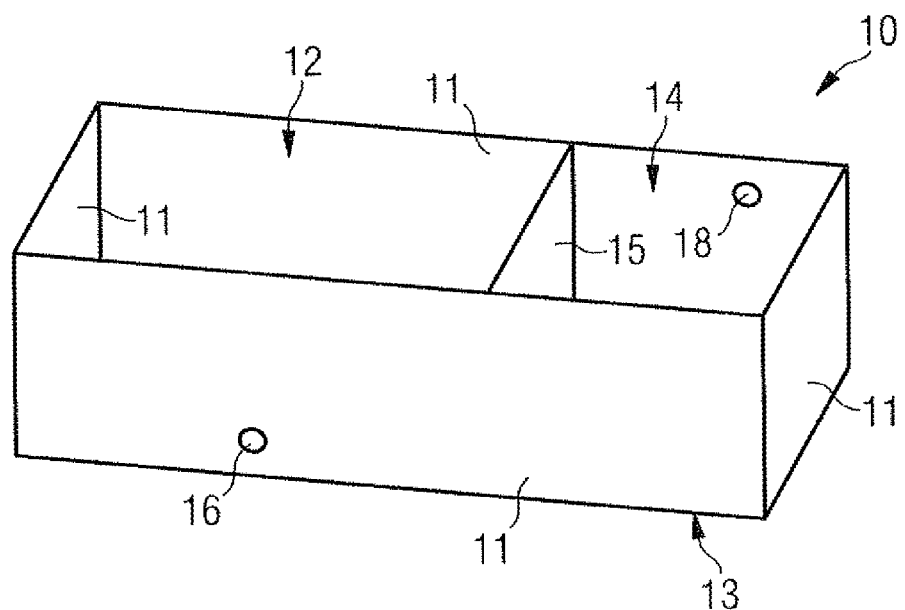
FIG. 1A, 1B schematically illustrate concentrate containers for preparing a medical fluid, according to embodiments of the invention.

FIG. 1A schematically illustrates a concentrate container 10 for preparing a medical fluid, according to an embodiment of the invention. The concentrate container 10 is in the present embodiment formed by four side walls 11 and a bottom wall 13. However, other spatial forms of the concentrate container 10 may be contemplated. Two concentrate compartments 12 and 14 are formed inside the container 10 by barrier means, which in the present embodiment is a partition wall 15 partially dividing the interior of the box into the two compartments 12 and 14. For instance, partition wall 15 may include an opening (not shown) for passing a fluid and solutes contained in the fluid. Concentrate compartment 12 includes an opening 16 as the medical fluid outlet, whereas concentrate compartment 14 is provided with an opening 18 forming a solvent inlet as the diluent inlet. Since partition wall 15 allows that fluids pass from compartment 14 to compartment 12, a solvent fed into compartment 14 through opening 18 may flow from compartment 14 into compartment 12, dissolve different concentrates contained in the different compartments and may leave the concentrate container 10 through opening 16.

The concentrates may be filled into the different compartments through the top openings of the concentrate compartments shown in FIG. 1A. In another example, the solvent inlets of concentrate container 10 may be formed simply by the top openings of the concentrate compartments and an opening 18 is not provided.

Hence, in one embodiment, a concentrate container for preparing a medical fluid, preferably for preparing a dialysis solution, includes at least two concentrate compartments, wherein at least one of the concentrate compartments has a medical fluid outlet, and at least one of the concentrate compartments has a diluent inlet. The compartments may be separated from each other in a permanent or semi-permanent manner. According to embodiments, the at least one medical fluid outlet and the at least one diluent inlet are separate from each other.

Embodiments of the invention allow for filling into each compartment a concentrate different from the concentrates of the other compartments and storing them substantially separate from each other. As a result, concentrate components for forming a medical fluid, such as dry concentrate components of a dialysate, may be filled, transported and stored in one container avoiding or without mixing the different components. This is especially useful for concentrate components which are liable to degradation and/or caking or clump together when intermixed. Further, the different concentrates or concentrate components can be dissolved or suspended using the concentrate container of embodiments, thereby forming a medical fluid or partial fluids of a medical fluid directly in the concentrate container in which they are provided or stored. Hence, the dilution, suspension or dissolution of the concentrates or concentrate components can be performed in different steps and/or in an efficient way, even for bicarbonate granules. Moreover, the concentrate container can be formed in a simple production process, by molding, and as just one disposable part.

Therefore, the concentrate container according to embodiments allows a physical separation between dry concentrates, a dissolution of the concentrates in different steps with a high efficiency, and an efficient waste disposal and can be formed by a simple production process. Moreover, using the concentrate container of embodiments, a medical fluid can be prepared in situ in a container, in which the concentrates can be stored and which can be directly coupled to a system for applying the medical fluid to a patient. Further, by performing a suitable dilution sequence for the different concentrate components, degassing and precipitation of concentrate components during dilution can be reduced or avoided. Consequently, a complete dissolution of the concentrate components or concentrates contained in the concentrate container can be achieved, in order to form the medical fluid.

In other examples of embodiments, the concentrate container has an angled or V-shaped inner surface. An example of a concentrate container having an angled inner surface is one of the concentrate containers 10 to 30. Each of them has edges, which promote during shaking of the concentrate container dissolution of the concentrates by the solvent.

Figure 1B:
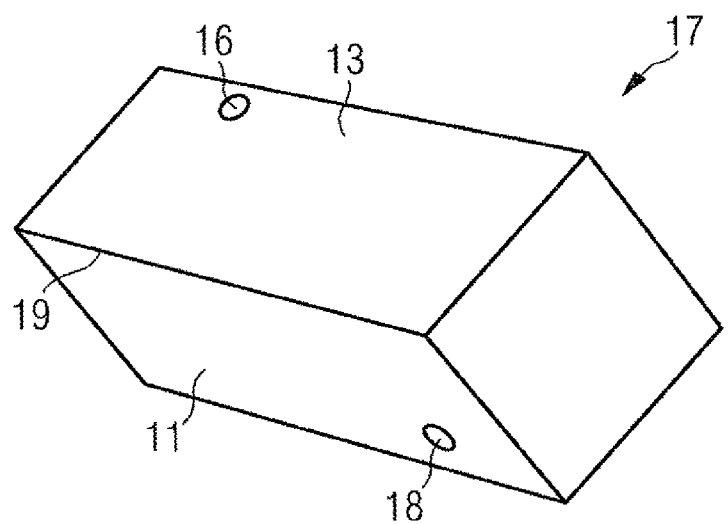

In one embodiment, the concentrate container has an angled or V-shaped inner surface and is adapted such that it is positionable and operable having the angle of the angled or V-shaped inner surface at the bottom. One example of this embodiment is concentrate container 17 shown in FIG. 1B in a perspective bottom view. Concentrate container 17 has a so-called tilted design. The medical fluid outlet 16 of concentrate container 17 as compared to concentrate container 10 is located in the bottom wall 13. Hence, an edge 19 of the concentrate container 17, which is formed by the bottom wall 13 and the sidewall 11 which includes the solvent inlet 18, is located between the solvent inlet 18 and the medical fluid outlet 16. As a result, the edge 19 between solvent inlet 18 and medical fluid outlet 16 is preferably filled with solvent, if the concentrate container 17 is held in a correspondingly tilted way such that the edge 11 is positioned at the bottommost position. In this arrangement of the concentrate container, the solvent and the concentrate filled in the container 17 accumulate in the angled part of the inner surface, i.e. in the present example in the V-shape of the edge 19 between the solvent inlet 18 and the medical fluid outlet 16, thereby promoting dissolution of the concentrate. Since in some embodiments, the concentrate container 17 is substantially rigid, the tilted design results in a high mechanical resistance, since a rigid edge can be positioned at the top. Further, the concentrate container 17 of the tilted design can easily and accurately be arranged on a correspondingly angled or V-shaped support. Moreover, a plurality of concentrate containers 17 can be stacked one above the other.

According to a further embodiment, a first concentrate compartment and a second concentrate compartment of the concentrate compartments are separated from each other by permanent barrier means, and each of the first and second concentrate compartments has a diluent inlet and a medical fluid outlet.

Figure 2A:
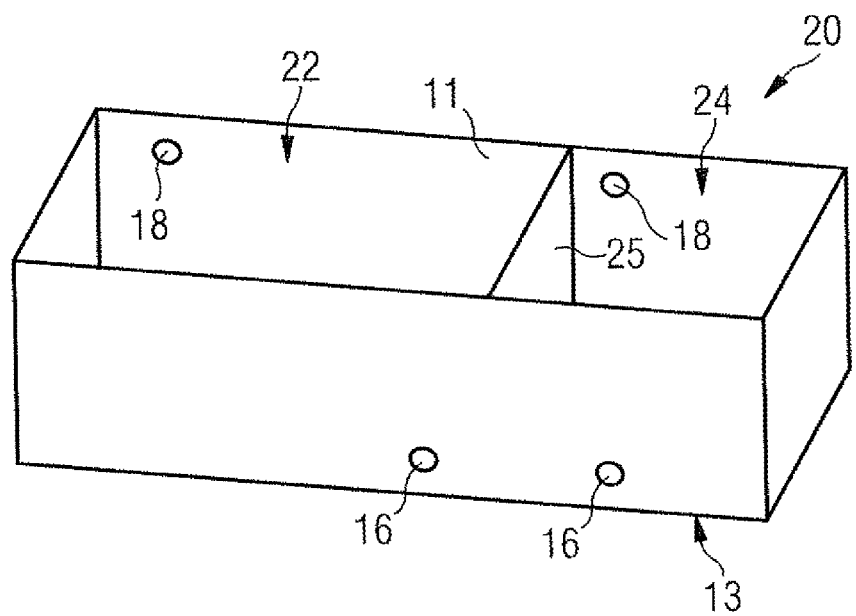
FIG. 2A, 2B schematically illustrate concentrate containers according to embodiments of the invention.

FIG. 2A schematically shows as an example of above further embodiment a concentrate container 20. Therein, compartments 22 and 24 are separated by a permanent barrier means, which in the present example is a wall 25 completely separating compartments 22 and 24. Further, compartments 22 and 24 each include one solvent inlet 18 and one medical fluid outlet 16.

In another embodiment, a first concentrate compartment and a second concentrate compartment of the concentrate compartments are separated from each other by releasable barrier means, e.g. a semi-permanent barrier, the first concentrate compartment has a diluent inlet and the second concentrate compartment has a medical fluid outlet. This embodiment is based on concentrate container 20 of FIG. 2A, wherein, however, wall 25 is replaced by a releasable barrier means (not shown), e.g. a plate slide which may be operated manually or automatically from outside of the concentrate container. Another example for a releasable barrier means is a piston valve (not shown) which can be opened by the diluent or solvent due to the fluid pressure and/or due to the flow of the diluent or solvent. Alternatively, the piston valve may be actuated from outside of the concentrate container.

According to a further embodiment, a first concentrate compartment and a second concentrate compartment of the concentrate compartments are separated from each other by permanent barrier means, and each of the first and second concentrate compartments has a diluent inlet and the first concentrate compartment has a medical fluid outlet; and a third concentrate compartment of the concentrate compartments is separated from the second concentrate compartment by releasable barrier means and has a medical fluid outlet.

Figure 2B:
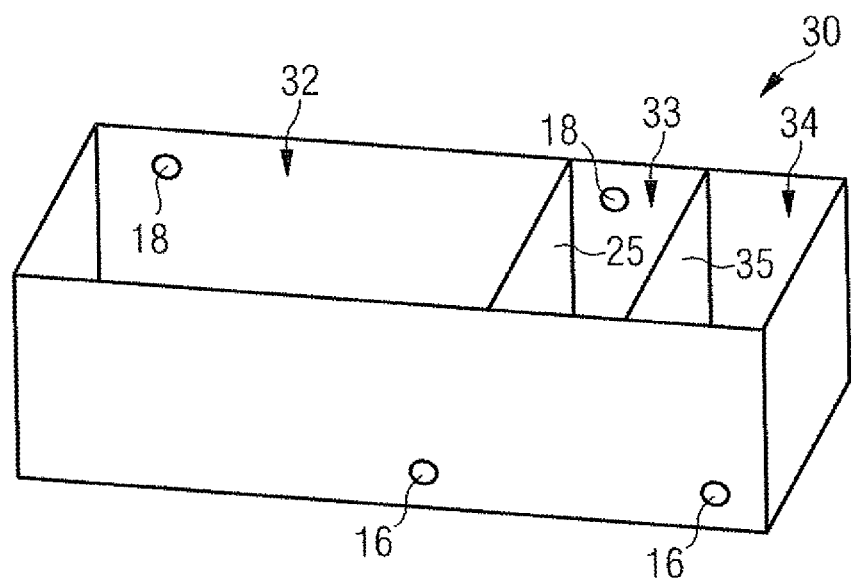

FIG. 2B schematically illustrates as an example a concentrate container 30 including three concentrate compartments 32, 33 and 34. Compartments 33 and 34 are separated by a releasable barrier means, which is in the present example a piston valve 35 which may be opened due to the flow and/or the fluid pressure of the diluent or solvent. Compartment 33 includes one solvent inlet 18 and compartment 34 includes one medical fluid outlet 16. Compartments 32 and 33 are separated by wall 25 as a permanent and complete barrier means. Compartment 32 further includes one solvent inlet 18 and one medical fluid outlet 16.

In embodiments described herein, one or more of the medical fluid outlets 16 may each be fluidly connected to a long channel having at least one outlet, e.g. a central outlet. An example of such an embodiment is illustrated in FIG. 3 in a top view. Therein, a concentrate container 300 is shown which is based on concentrate container 30 of FIG. 2B. Concentrate container 300 further includes a channel 150 extending along the sidewall 11 in which the medical fluid outlets 16 of the concentrate container are formed. The channel 150 has a central outlet 160 through which the two fractions of the medical fluid originating from medical fluid outlet 16 of the compartment 32 on the one hand and from medical fluid outlet 16 of the compartments 33 and 34 on the other hand can pass and combine. Thereby, connectivity to a medical fluid transfer line is simplified, since just one medical fluid transfer line is required and can be connected to the central outlet 160 of the concentrate container 300.

The material of the concentrate containers may, according to embodiments, include Polyamide or Polyethylene, e.g. PEHD. The concentrate container may be formed by injection molding. The internal volume of the concentrate container compartments may be in a range to contain concentrates for the preparation of aimed volume of the medical fluid. For the preparation of a 60 l batch of dialysis fluid a concentrate container volume of 2 l is in some examples sufficient. This depends on the kind of diluents which may already contain several solutes. These solutes then do not have to be provided by concentrates in the concentrate container. In general a concentrate volume of 0.5 to 3 l may be appropriate for a broad range of applications. The concentrate container according to embodiments may be formed from a material including Polypropylene (PP), Polyethylene terephalate (PET), Polyurethane (PU), Polysulfone (PSU), Polyvinylchloride (PVC), Polyethylene (PE), Polystyrene (PS), Polyalphaolefins, Copolymers of propylene, ethylene, butylenes, octane, Polymer blends of the aforementioned Polymers.

Further, the concentrate container of embodiments may have at least one fluid transmission means. The fluid transmission means is sealed off from the compartments. An example of a container 40 having a fluid transmission means is shown in FIG. 4. Concentrate container 40 includes a tube 49 as fluid transmission means passing through compartment 12 and allowing passage of fluids through compartment 12 without mixing with concentrates, suspensions or fluids contained in compartment 12. The inner lumen of the fluid transmission means may be in a range from 3 to 20 mm, the wall thickness of the fluid transmission means may be from 1 to 2.5 mm.

In a further embodiment, the first concentrate compartment includes at least one restrictor means or at least one restrictor means subdividing the first concentrate compartment into sub-compartments. For instance, as shown in FIG. 5, concentrate compartment 12 includes a partial wall 52 allowing passage of a fluid or of a concentrate between two sub-compartments 53 and 54 separated by partial wall 52. The restrictors promote diluting and/or dissolving the concentrates during filling of diluent into the first concentrate compartment, since they increase the water speed and the turbulences. At least one of the restrictors can be or include a nozzle or a frit, which may cause turbulences.

According to examples of embodiments, the concentrate container includes at least one filter means provided at the at least one medical fluid outlet and/or at the at least one diluent inlet. For instance, in the concentrate container shown in FIG. 5, a filter means 55 is provided at solvent inlet 18. A further filter means (not shown in FIG. 5) may be installed at medical fluid outlet 16 of compartment 12. Thereby, outflow of undissolved particles out of the concentrate container can be avoided. Furthermore, a filtering of the medical fluid or dialysate can be achieved. The filter means can be formed from a material including Polyethylene. In one example, the filter means 55 is a microporous filter from Porex having an average porosity of 180 to 300 µm and a thickness of 2.9 mm. For example, the filter can be a sterile filter with average pore size of 0.22 µm to 5 µm.

The concentrate container of embodiments may include a lid or a sealable lid, adapted to close at least one of the concentrate compartments. An example of such an embodiment is shown in FIG. 6, wherein concentrate container 60 includes a lid 61 for closure of all compartments. Thereby, contamination of concentrates contained in the closed concentrate compartments may be prevented. Further, concentrate container 60 may be shaken or tilted without loss of concentrates and/or diluent contained. Lid 61 may be a 6 mm thick Poly(methyl methacrylate) (PMMA) window hinged to one sidewall 11 of the concentrate container. According to another example, the lid may be formed from a Polyamide/Polyethylene (PA/PE) foil welded on the concentrate container. Further, a PA/PE foil can be applied as a lid. In one embodiment PA/PE foil is formed from a two-layer or multilayer film, whereby one layer is formed from PE Polymers for welding purposes. The other layer is formed from PA Polymers for establishing a high tear resistance and adequate gas barrier of the multilayer film. The multilayer thickness may be about 200 µm and the dimension of the lid may be about 40.times.10 cm depending on concentrate container dimensions.

According to one embodiment, a system for preparing a medical fluid, preferably for preparing a dialysis solution, is provided, the system including a concentrate container according to embodiments described herein, a fluid container fluidly connected to a medical fluid removal line, at least one fluid transfer line fluidly connecting the at least one medical fluid outlet of the concentrate container and the fluid container.

The system for preparing a medical fluid, according to embodiments, allows a physical separation between dry concentrates, a dissolution of the concentrates in different steps with a high efficiency, and an efficient waste disposal. Further, the parts of the system can be formed by simple production processes and the system can easily be assembled and disassembled. Moreover, using the system of embodiments, a medical fluid can be prepared in situ in a container, in which the concentrates have been stored and while the container is provided in the system.

Figure 7:
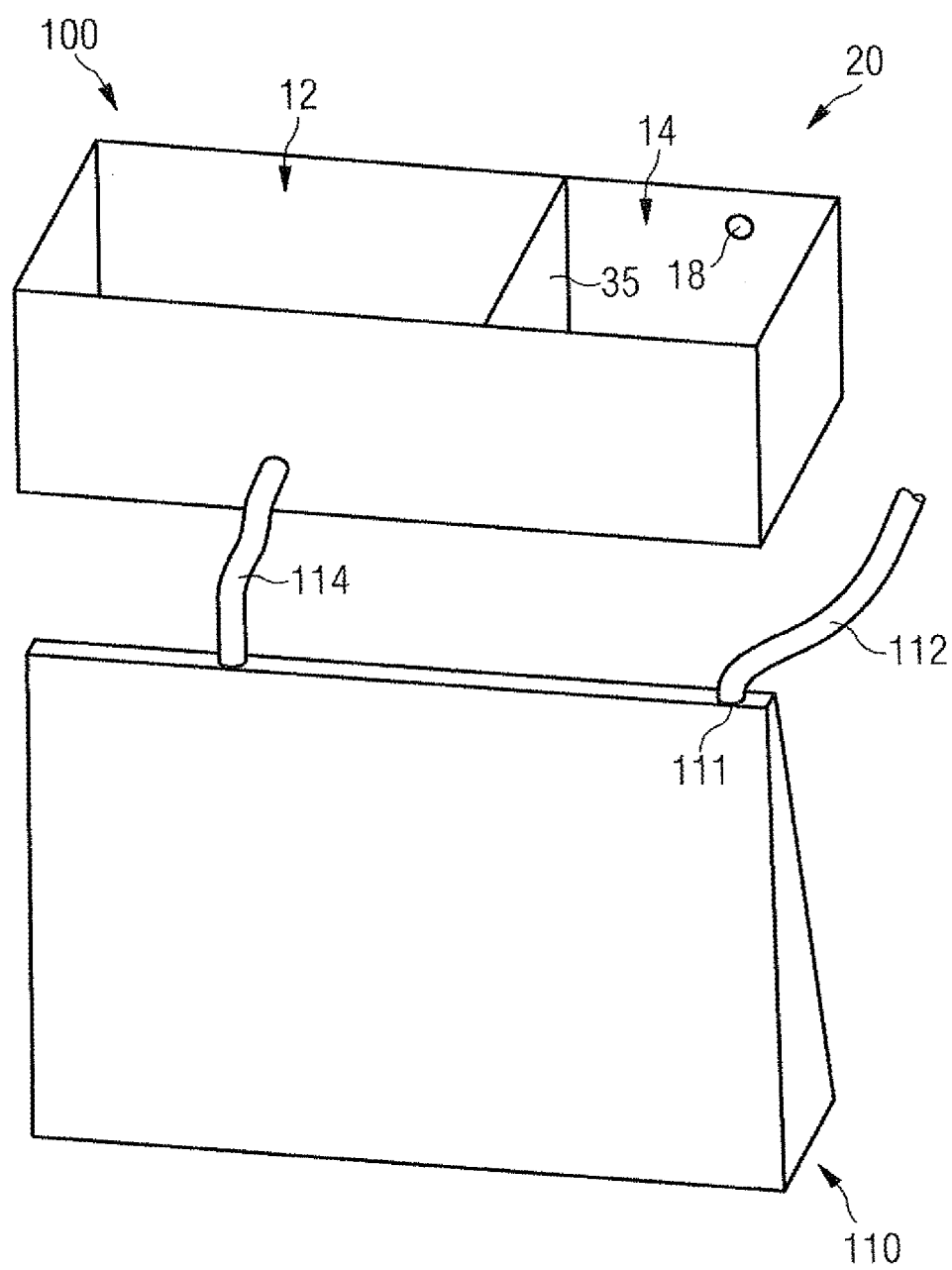
FIG. 7 schematically illustrates a system for preparing a medical fluid, according to an embodiment of the invention.

FIG. 7 illustrates a system 100 as an example of a system for preparing a medical fluid according to embodiments. System 100 includes concentrate container 20 of FIG. 2A, wherein wall 25 is replaced by a releasable barrier means 35, e.g. a plate slide which may be opened and closed. In addition, system 100 has a fluid container 110 which is fluidly connected to concentrate container 20 via a fluid transfer line 114. In the present example, fluid transfer line 114 is a tube connecting medical fluid outlet 16 of the concentrate container 20 and fluid container 110. The latter is shown in FIG. 7 as a non-transparent bag. Fluid container 110 has an opening, which in the present example is the medical fluid drainage line 111 and is fluidly connected to a medical fluid removal line 112 for withdrawing a medical fluid collected in fluid container 110. According to other embodiments, the medical fluid drainage line 111 may include a tube extending into the interior of the fluid container. In this example, the internal volume of the concentrate container compartments may be in a range to contain concentrates for the preparation of aimed volume of the medical fluid. For the preparation of a 60 l batch of dialysis fluid a concentrate container volume of 2 l is in some examples sufficient. This depends on the kind of diluents which may already contain several solutes. These solutes then do not have to be provided by concentrates in the concentrate container. In general a concentrate volume of 0.5 to 3 l may be appropriate for a broad range of applications. The third container 110 may have an inner dimension of about 70 l.

For forming a medical fluid, concentrate container 20 including releasable barrier means 35 is provided with two different concentrates, e.g. dry concentrates, separately contained in concentrate compartments 12 and 14. A solvent is introduced through opening 18 into compartment 14, dissolving and/or suspending the concentrate provided in compartment 14.

Then, the solvent including dissolved and/or suspended concentrate from compartment 14 passes into compartment 12 after release of the barrier means 35, thereby dissolving and/or suspending the concentrate contained therein. Thereafter, a medical fluid formed by the solvent and the concentrates dissolved or suspended therein leaves concentrate compartment 12 through opening 16 and fluid transfer line 114 and is collected in fluid container 110. The medical fluid may then be withdrawn from fluid container 110, e.g. by a pump installed in medical fluid removal line 112.

Examples of diluents or solvents used in embodiments described herein are diluents for forming medical fluids, such as water from Reverse Osmosis (RO) processing, diluted solutions which contain solutes or parts of solutes necessary for the final concentrated medical solution. The amounts of diluents used in examples correspond to the final volumes of the medical solutions to be prepared. The preparation of volumes of diluents may be adapted depending on the solution volume to be prepared. For example, solution volumes may be 2-120 l, 5 to 80 l, preferred 30 to 80 l, more preferred 50 to 70 l.

In the example of FIG. 7, solvent inlet 18 may be connected to a solvent feed line 118 as a diluent feed line, as shown in FIG. 8. Hence, according to embodiments, at least one diluent inlet of the concentrate container is fluidly connected to a diluent feed line.

Further, according to embodiments, at least one of the concentrate container, the fluid container and the fluid container system is tiltably and/or removably installable or tiltably and/or removably installed in the system. By tilting the concentrate container, dissolution of the concentrates in the solvent may be promoted. Further, because the concentrate container and/or the fluid container(s) are removable, a simple replacement of the containers is feasible, in order to provide fresh concentrates contained in the concentrate container, and/or in order to avoid contamination of the system by providing fresh containers.

According to further examples of embodiments, the fluid container may include a medical fluid drainage line 111, which may include a tube (not shown in FIG. 7) and an opening at the top of the fluid container, the tube extending from the opening to the bottom of the fluid container. Thereby, withdrawal of the medical fluid from the fluid container is easier.

In another embodiment, the system may include another fluid container connected to a consumed medical fluid collection line, the fluid container being insertable into the another fluid container. An example of this embodiment is illustrated in FIG. 8 as part of an embodiment of a system 101 having the concentrate container 10 of FIG. 1A fluidly connected via fluid transfer line 114 to fluid container 110 shown in FIG. 7. The concentrate container 10 further has the solvent feed line 118 connected to solvent inlet 18 as an optional feature. In addition, another fluid container 120 is provided encompassing fluid container 110. In FIG. 8, fluid container 120 is transparent, but is not restricted thereto according to embodiments described herein. Fluid container 120 is fluidly connected to a tube 122 which is a consumed medical fluid collection line, which is for instance connected to a dialysis machine (not shown). As an optional feature, fluid container 120 includes a tube 121 fluidly connected to tube 122, for guidance and/or withdrawal of consumed medical fluid into/out of the fluid container 122.

Figure 9A:
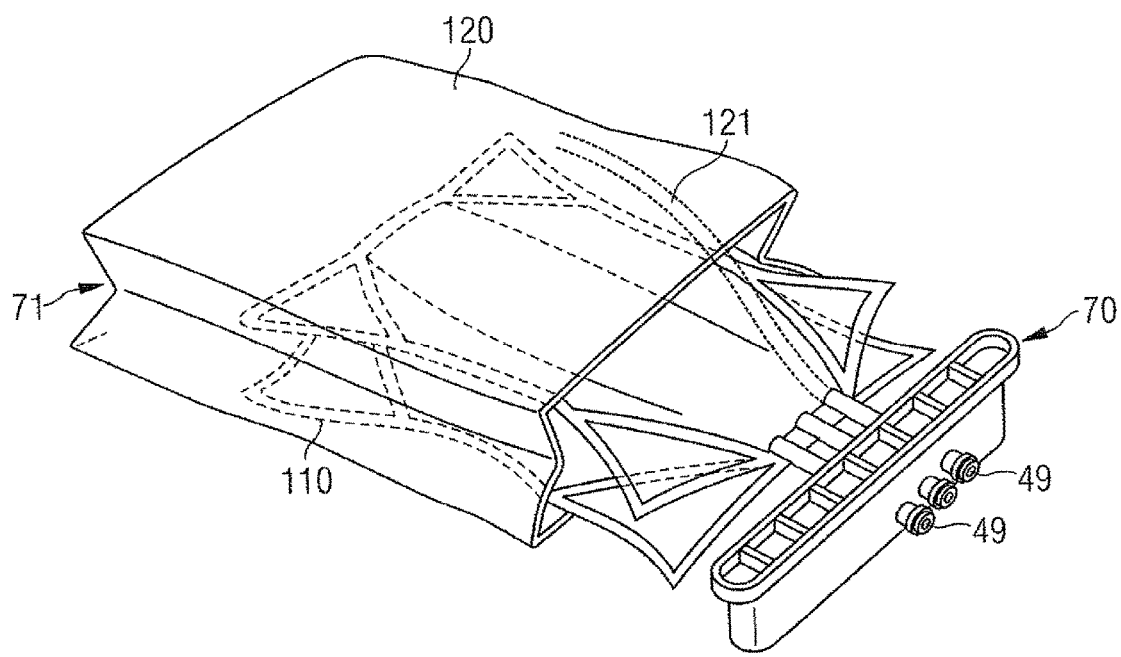
FIG. 9A schematically illustrates a system for preparing a medical fluid, according to an embodiment of the invention.

The concentrate container of the system for preparing a medical fluid, according to embodiments, may have at least one fluid transmission means, one of the fluid transmission means being connectable or weldable to the medical fluid drainage line and/or another one of the fluid transmission means being connectable or weldable to the consumed medical fluid collection line. An example of this embodiment is shown in FIG. 9A, wherein a concentrate container 70 has two fluid transmission means 49, one of which is fluidly connected to the medical fluid drainage line 111 of the fluid container 110 and another one of which is fluidly connected to tube 121 provided in fluid container 120. A port of the concentrate container shown in FIG. 9A, the port positioned between the two fluid transmission means 49, may be a solvent inlet.

In FIGS. 9A, 9B, 9C, 9D, 10A and 10B, the fluid containers 110 and 120 are illustrated as transparent bags, but according to embodiments described herein the fluid containers are not restricted thereto.

Materials and dimensions of tubes used for fluid transfer line 114, consumed medical collection line 122, medical fluid drainage line 112, solvent feed line 118 may include PP, Styrene block copolymers from Styrene butadiene, ethylene, isoprene (SEBS; SIS; SEPS), PVC, silicone, PE, Polyalphaolefines.

Figure 10A:
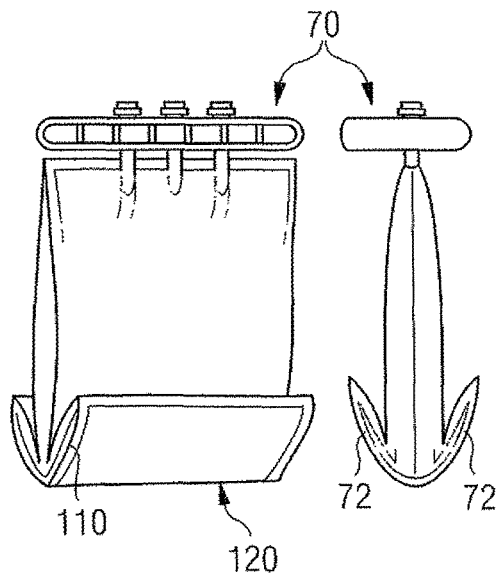
FIG. 10A, 10B schematically illustrate a system for preparing a medical fluid, according to an embodiment of the invention.
Figure 10B:
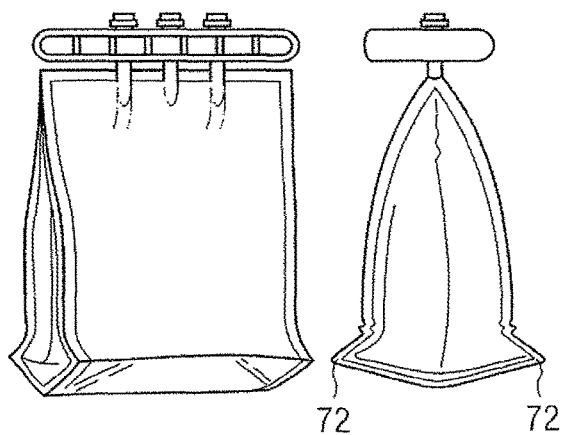

According to embodiments, the concentrate container may be positioned at the top or at the bottom of at least one of the fluid container and of the another fluid container. An example of the concentrate container positioned at the top of at least one of the fluid containers is shown in FIGS. 10A and 10B. If the concentrate container is positioned below the fluid container(s), inside of the fluid container no tubes are necessary for drainage or for agitation.

Figure 11:
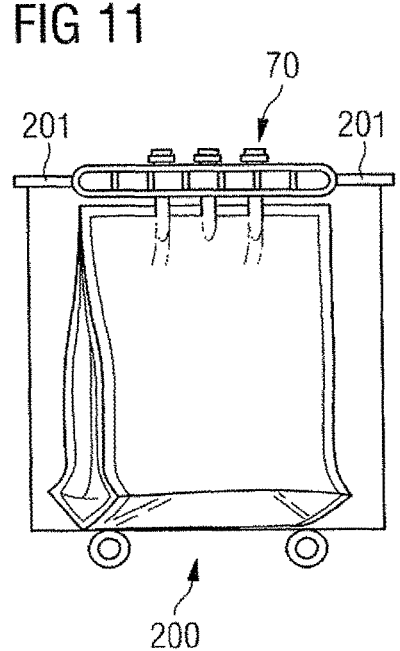
FIG. 11 schematically illustrates a system for preparing a medical fluid, according to an embodiment of the invention.

In further examples of embodiments, the system for preparing a medical fluid includes a transport means adapted to support and/or to include at least one of the concentrate container, the fluid container and the another fluid container, as schematically illustrated in FIG. 11. Therein, according to an example, as a transport means a trolley 200 is schematically shown, which includes the fluid container system arranged at the concentrate container as shown in FIGS. 10A and 10B. For instance, the trolley 200 may be a transparent container having bottom wheels. For installation, the concentrate container 70 may include supports 201 for mounting at the top of the trolley 200. Thereby, the system for preparing a medical fluid can be used location-independently at any time. The trolley 200 may be adapted for transporting high amounts of solution, such as about 50 to 100 l, e.g. about 72 l.

In examples of embodiments, the system for preparing a medical fluid may be adapted to be a mobile and/or modular system. Further, the concentrate container, the fluid container, the another fluid container and/or the transport means may be modular components of the system. Moreover, the concentrate container may be substantially rigid or substantially non-flexible. In some embodiments, the fluid container and the another fluid container are substantially flexible, for instance flexible pouches.

The fluid container and/or the another fluid container of embodiments described herein can have an internal capacity of about 60 to 70 liters, in order to accommodate high volumes of fluids. The another fluid container can in some examples be also used for accommodating ultra filtrate from a patient.

The fluid container and the another fluid container of embodiments described herein can each be formed from PET, PA, PE, PP, PVC, preferably as multi layered films. For instance, the fluid container and the another fluid container can be formed from a multi layered film including PA or PET and PE. Thereby, an excellent weldability of the inner layers of the container films and a superior compatibility with medical solutions can be achieved.

In some embodiments, at least two different components of a concentrate, e.g. components of a dry concentrate, are provided in different concentrate compartments of the concentrate container. For instance, each concentrate component is filled in a concentrate compartment of its own. Thereby, a mixing of different concentrates, e.g. different dry concentrates, contained in different concentrate compartments can be avoided during providing and storing the concentrates in the compartments. Further, degradation and caking of components of the dialysate can be prevented or at least reduced.

For instance, one of the concentrate compartments, e.g. the second or third compartment, includes glucose, preferably separately from other concentrate components. Further, at least two different other concentrate components filled in the concentrate container include at least one element chosen from sodium bicarbonate, sodium chloride, magnesium chloride, potassium chloride, calcium chloride, and citric acid. For instance, a first component of a concentrate includes sodium bicarbonate and sodium chloride, a second component of the concentrate includes sodium chloride, magnesium chloride×6 $H_2O$, potassium chloride, calcium chloride×6 $H_2O$, and anhydrous citric acid, and a third component of the concentrate includes glucose×$H_2O$.

In one example of a concentrate container, the first compartment contains granules formed of 37% NaCl and 63% sodium bicarbonate, e.g. 515 g, the second compartment contains monohydrate glucose, e.g. 66 g, and the third compartment contains minor ions and citric acid, e.g. 75 g. Minor ions are, for instance, NaCl, KCl, $MgCl_2$, $CaCl_2$. In a variation of this example, the contents of the second and third compartment can be exchanged, such that the second compartment contains minor ions and citric acid, and the third compartment contains monohydrate glucose. Minor ions are for instance ions of minor concentration present in dialysis fluid compared to bicarbonate ions or sodium ions.

According to an example, a first component of a dry concentrate includes 187.5 g sodium bicarbonate and 327.5 g sodium chloride; a second component of the dry concentrate includes 35 g sodium chloride, 6.1 g magnesium chloride×6 $H_2O$, 8.95 g potassium chloride, 13.2 g calcium chloride×6 $H_2O$, and 11.5 g anhydrous citric acid; and a third component of the dry concentrate includes 66 g glucose×$H_2O$. The first to third components may be provided separately in different compartments of the concentrate container of embodiments. By addition of a corresponding amount of RO water to the first to third components and combining the resulting solutions, a dialysate is obtained which is useful for hemodialysis, having the following ratio of components: $Na^+:K^+:Mg^{2+}:Ca^{2+}:Cl^-:HCO_3^-=140:2:0.5:1.5:108:35$.

According to embodiments, glucose may be provided separately in one of the compartments of a concentrate container for forming a dialysate. If glucose is provided in admixture with dry bicarbonate, it may be degraded, resulting in byproducts which may have undesired effects when administered to patients. Caking of glucose admixed with other components of the dialysate further typically causes an imperfect dissolution of the components in RO water. Using embodiments described herein, these undesired effects can be prevented.

In a further embodiment, a fluid container system for preparing a medical fluid, preferably for preparing a dialysis solution, is provided, including a fluid container for collecting a prepared medical fluid, the fluid container having a medical fluid drainage line, and another fluid container for collecting a consumed medical fluid, the fluid container being insertable into the another fluid container. The medical fluid drainage line may include an opening, a port and/or a tube, each adapted for drainage of the medical fluid from the fluid container.

Figure 9B:
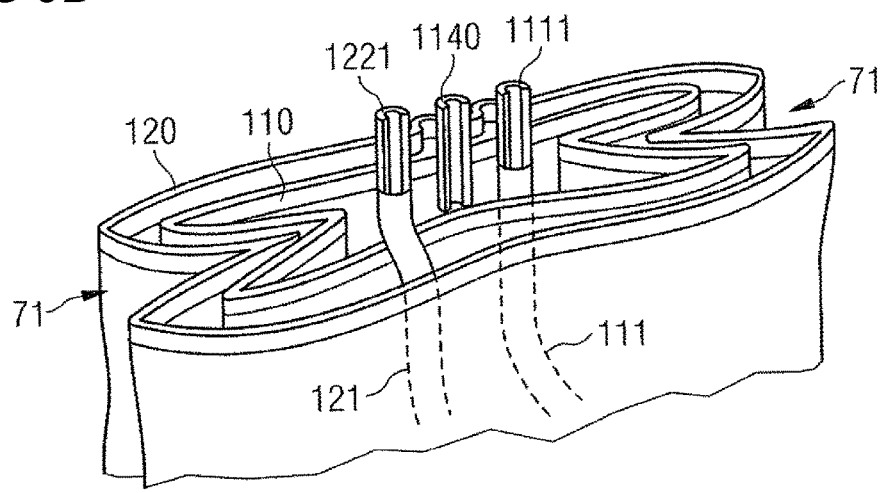
FIG. 9B schematically illustrates a fluid container system for preparing a medical fluid, according to an embodiment of the invention.

An example of this embodiment is described above referring to the two fluid containers 110, 120 shown in FIG. 8. FIG. 9B illustrates another example of this embodiment, wherein the fluid container 110 and the fluid container 120 are flexible transparent plastic bags. These bags may further be disposables for easy maintenance of a contamination-free system. As shown in FIG. 9B, the bags 110 and 120 may each have gussets 71 on each side of the bag. Bag 120 has a higher internal volume than the bag 110, such that the latter can be inserted into bag 120. FIG. 9A illustrates the fluid container system illustrated in FIG. 9B mounted at concentrate container 70.

FIGS. 10A and 10B show another example of a fluid container system of embodiments, wherein the two fluid containers 110 and 120 each include a bottom including two outwardly bendable folds. This example is useful if the fluid container and the another fluid container are flexible bags which have to be put on a rigid support, such as a transport means, for instance because of a high weight of the contents filled in the fluid containers. Thereby, reduced fluid volumes can be stored inside the bags, since the spatial volume of the bags can also be reduced due to the bendable fold and their flexibility. Further, the bags can be opened symmetrically and homogeneously during filling. In addition, a constant height of the bags during filling and use can be maintained.

In this example the fluid container system may also be mounted at concentrate container 70. FIG. 10A shows the fluid container system of this example having the folds bent upwards, whereas FIG. 10B illustrates the fluid container system having the folds bent sidewards.

Hence, in examples of the fluid container system at least one element chosen from the fluid container and the another fluid container may be a flexible container, a disposable, a bag, e.g. a stand-up-pouch, a bag having a gusset on each side and/or a bag having a bottom including two outwardly bendable folds.

According to further embodiments, the medical fluid drainage line and/or the another fluid container may each include a tube extending into the interior or to the bottom of the respective fluid container. In some examples, the tube may include at its free end inside the respective container a nozzle as a restrictor, e.g. for producing turbulences. The material of the tube may include PP, Styrene block copolymers from Styrene butadiene, ethylene, isoprene (SEBS; SIS; SEPS), PVC, silicone, PE, Polyalphaolefines. Thereby, withdrawal of fluids from the fluid containers is facilitated and the tubes further may provide agitation of the fluid inside of the fluid containers. The tube of medical fluid drainage line 111 and the tube of the another fluid container 120 are shown e.g. in FIG. 9A.

In embodiments, the fluid container includes at least one first line connection means for at least one fluid transfer line and a second line connection means which is connectable to, connected to or included in the medical fluid drainage line.

In further embodiments of the fluid container system described herein, the inner fluid container includes a first line connection means 1140 for the fluid transfer line 114 and a second line connection means 1111 included in the medical fluid drainage line 111, and/or the outer fluid container includes at the tube a third line connection means 1221 for the consumed medical fluid collection line, as shown in FIG. 9B. This allows an easy interconnection of the fluid container and the another fluid container with the concentrate container via the fluid transfer line 114, with medical fluid removal line 112 and/or with consumed medical fluid collection line 122. The material of the line connection means may include PP, Styrene block copolymers from Styrene butadiene, ethylene, isoprene (SEBS; SIS; SEPS), PVC, silicone, PE, Polyalphaolefines.

In embodiments, the concentrate container may have a channel being fluidly connected to one or more of the medical fluid outlets and having at least one outlet.

Figure 9C:
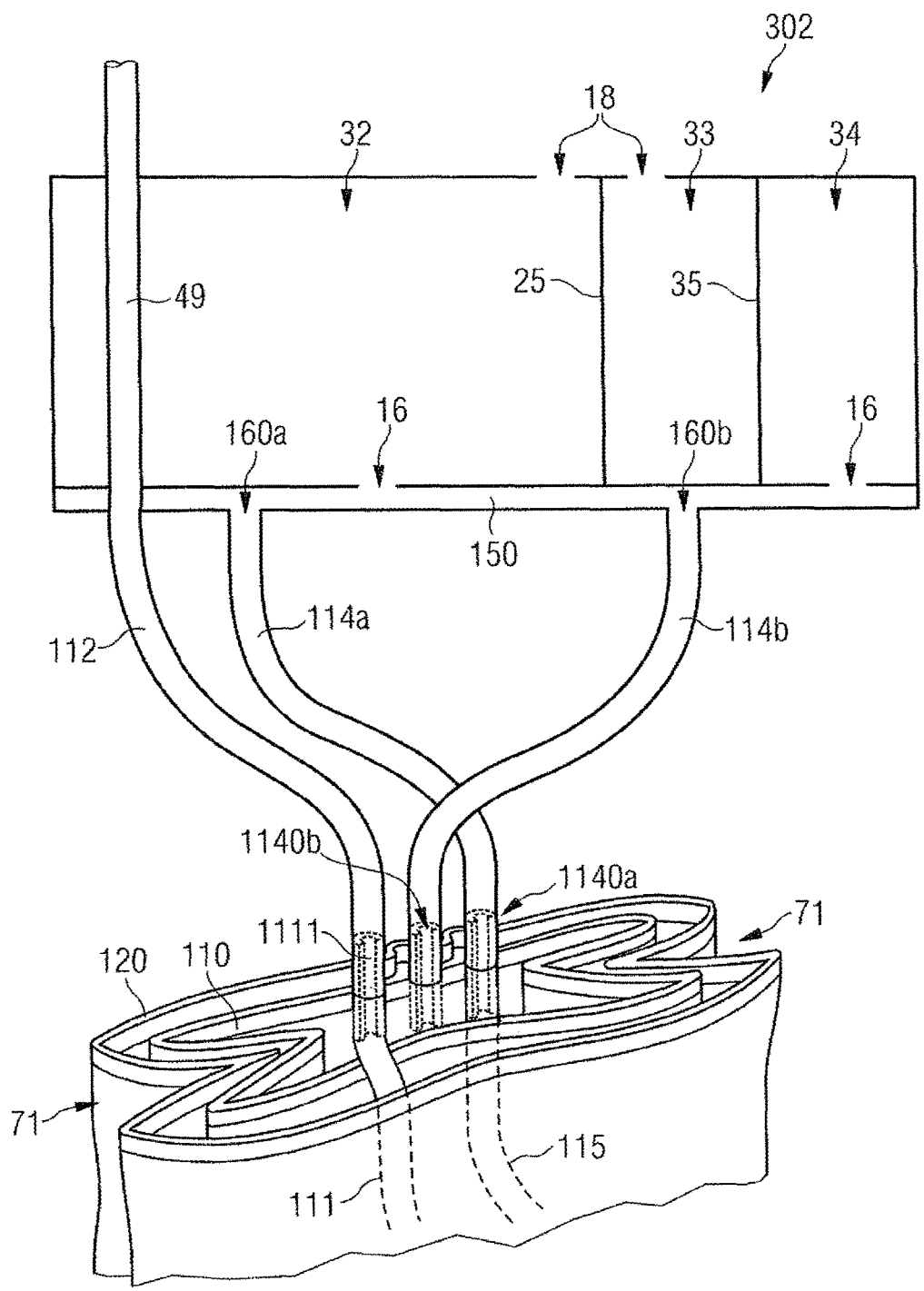
FIG. 9C schematically illustrates a fluid container system for preparing a medical fluid, connected to a concentrate container, according to an embodiment of the invention.

According to another embodiment, the inner fluid container 110 includes two first line connection means 1140a and 1140b for two fluid transfer lines 114a and 114b and a second line connection means 1111 included in or connected to the medical fluid drainage line 111, as shown in FIG. 9C. Line connection means 1140a may be connected to a tube 115 extending to the bottom of the inner fluid container, as shown in FIG. 9C. In the present embodiment, the inner fluid container 110 is connected to a concentrate container 302, which differs from concentrate container 300 shown in FIG. 3 in that instead of the central outlet 160, two outlets 160a and 160b are provided in channel 150. Outlet 160a is connected via fluid transfer line 114a and line connection means 1140a to the inner fluid container 110. Outlet 160b is connected via fluid transfer line 114b and line connection means 1140b to the inner fluid container. Further, concentrate container 302 has a tube 49 as fluid transmission means passing through compartment 32 and allowing passage of fluids through compartment 32 without mixing with concentrates, suspensions or fluids contained in compartment 32. In the present embodiment, medical fluid drainage line 111 is fluidly connected via second line connection means 1111 and medical fluid removal line 112 to tube 49 for passage of drained medical fluid through concentrate container 302. The outer fluid container 120 may include at its tube (not shown) a third line connection means for the consumed medical fluid collection line (not shown in FIG. 9C). This embodiment allows an easy interconnection of the fluid container with the concentrate container via two fluid transfer lines and one medical fluid removal line.

In some embodiments, the concentrate container includes a first channel being fluidly connected to one of the medical fluid outlets and having an outlet, and a second channel being fluidly connected to another one of the medical fluid outlets and having another outlet, wherein the first and the second channels are fluidly separated by separating means.

Figure 9D:
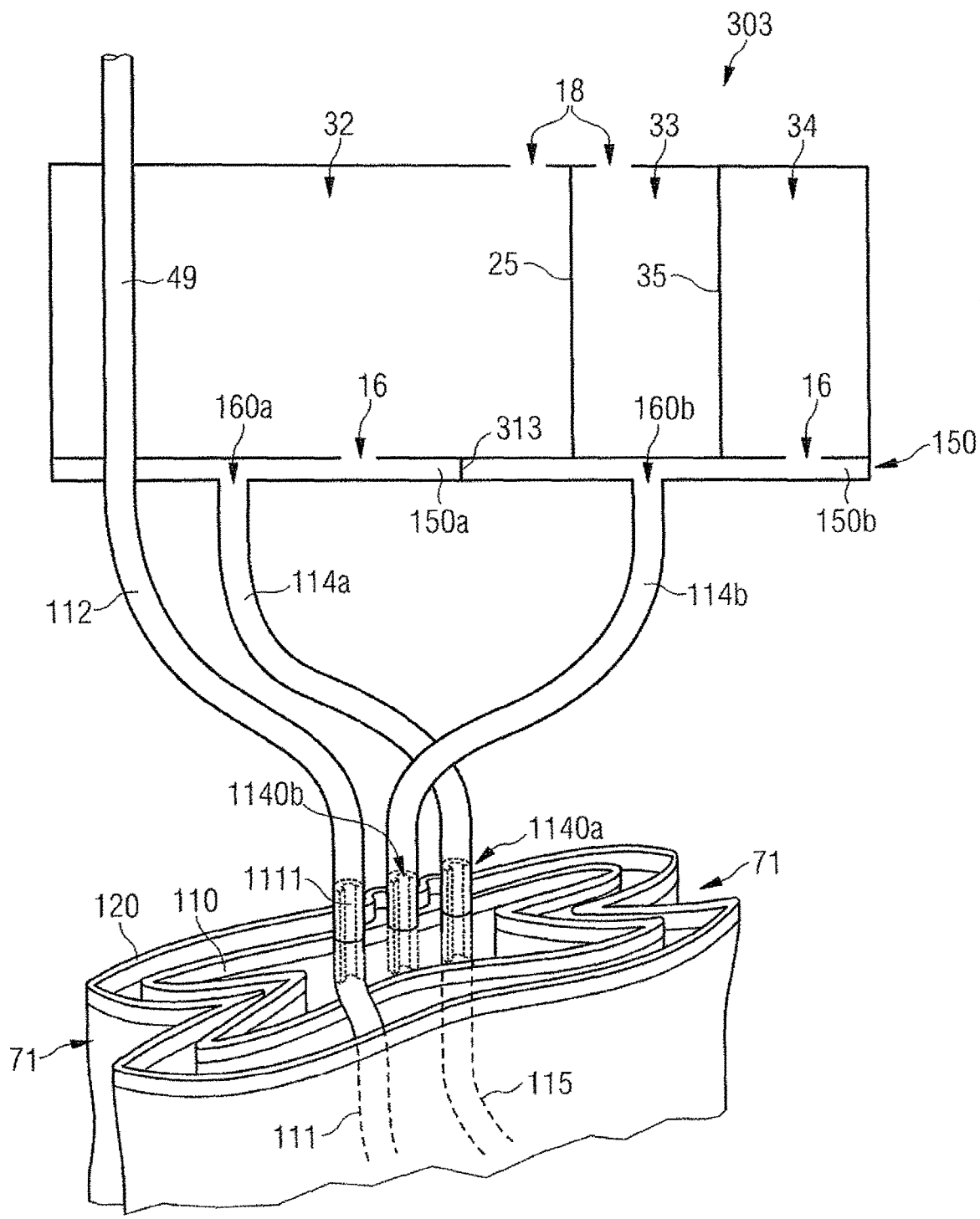
FIG. 9D schematically illustrates a fluid container system for preparing a medical fluid, connected to a concentrate container, according to an embodiment of the invention.

FIG. 9D illustrates a further embodiment of a system for preparing a medical fluid, including a concentrate container 303 according to an embodiment. The system of FIG. 9D differs from the system of FIG. 9C in that the inner fluid container 110 is connected to a concentrate container 303. The concentrate container 303 differs from the concentrate container 302 of FIG. 9C in that channel 150 has a separating means 313 between the outlets 160a and 160b. Thereby, channel 150 is subdivided into two separate channels 150a and 150b. The separating means 313 may be a separating wall or a separating strip, which completely separates the fluids passing through openings 16 into outlets 160a and 160b from each other. This means that the fluid originating from concentrate compartment 34 and flowing through outlet 160b is not mixed with the fluid originating from concentrate compartment 32 and flowing through outlet 160a. Thereby, an undesired gas formation caused by intermixing of the two fluids is prevented. Such gas formation may hinder or prevent discharge of the concentrates and/or of the fluids containing the concentrates from channel 150.

For instance, using concentrate container 303 of the present embodiment, $CO_2$ gas evolution due to contact or mixing of a fluid, which contains bicarbonate and originates from concentrate compartment 32, and a fluid, which contains an acid and originates from concentrate compartments 33 and 34 is avoided and/or prevented inside channel 150 and inside fluid transfer lines 114a and 114b due to separating means 313.

Further, using the embodiment of the system of FIG. 9D, the fluid containing bicarbonate and originating from compartment 32 may be directed via fluid transfer line 114a and tube 115 to the bottom of inner fluid container 110. The fluid containing an acid and originating from compartments 33 and 34 may be directed through fluid transfer line 114b and first line connection means 1140b into inner fluid container 110 from above. Thereby, $CO_2$ gas evolution caused by contact or mixing of the two fluids happens in the inner fluid container 110. Moreover, guiding the fluid which contains bicarbonate to the bottom of the inner fluid container 110 and adding the fluid which contains the acid from above results in a quick intermixing of the two fluids. This allows avoiding or preventing local variations of the concentrations of the dissolved concentrates. The $CO_2$ gas developed by mixing the two fluids can be discharged through medical fluid removal line 112 or through another port of the inner fluid container 110, in order to depressurize.

A further embodiment is directed to a kit of parts for preparing a medical fluid, including at least two elements chosen from the concentrate container according to any example or embodiment described herein, a fluid container, the fluid container system according to any example or embodiment described herein, and a transport means adapted to support and/or to include at least one of the concentrate container, the fluid container, and the fluid container system. The transport means of the kit of parts can be the trolley 200 shown in FIG. 11.

The concentrate container, the kit of parts and/or any system according to embodiments described herein may be used in dialysis, acute dialysis, hemodialysis, hemodiafiltration, peritoneal dialysis, or for preparing a dialysis solution.

A yet further embodiment is directed to a method for preparing a medical fluid, preferably for preparing a medical fluid or a dialysis solution in a system for preparing a medical fluid according to any embodiment described herein, the method including providing a concentrate container including at least one concentrate compartment, wherein a first compartment of the concentrate compartments contains a first concentrate component; feeding a diluent into the first compartment; rinsing the first compartment by the diluent and diluting the concentrate component; and transferring the diluted first concentrate component into a fluid container. Thereby, undesired contamination or degradation of the concentrate component contained in the first concentrate compartment of the concentrate container may be avoided.

In the method of embodiments, the concentrate container may further include a second concentrate component in a second compartment of the concentrate compartments; the method further including feeding the diluent into the second compartment; rinsing the second compartment by the diluent and diluting the second concentrate component; and transferring the diluted second concentrate component into the fluid container. That means that different concentrate components contained in two different compartments of the concentrate container may be diluted, dissolved or suspended individually and without mixing, and/or one after the other.

Moreover, in an example of the method according to embodiments, each of the first and second compartments may be separately fed with the diluent and rinsed. In other embodiments, the feeding and rinsing of the second compartment may be performed by passing the diluent from the first compartment into the second compartment. This may, for instance, be achieved by passing the diluent through an opening between the first and the second compartment or by releasing a releasable barrier means between the first and second compartment.

In some embodiments, the concentrate container further includes a third compartment containing a third concentrate component, each of the first and second compartments is separately fed with the diluent and rinsed, and the feeding and rinsing of the third compartment and the diluting of the third concentrate component is performed by passing the diluent from the second compartment into the third compartment, e.g. by opening a releasable barrier means between the second and the third compartment. For instance, the concentrate container further includes a third compartment containing a third concentrate component; each of the first and second compartments is separately fed with the diluent and rinsed; and the method further includes, before transferring the diluted second concentrate component into the fluid container, feeding the diluent into the third compartment by opening a releasable barrier means between the second and the third compartment and passing the diluent from the second compartment into the third compartment, and rinsing the third concentrate compartment and diluting the third concentrate component. Thereafter, the diluted second and third concentrate components are transferred into the fluid container.

For instance, the first and second concentrate compartments are separated by permanent barrier means and the second and third concentrate compartment are separated by releasable barrier means. The latter may be a piston valve which can be opened due to the flow and/or the fluid pressure of the diluent. In one example, into the first compartment containing sodium bicarbonate as a concentrate component, RO water is introduced in a first step and sodium bicarbonate is dissolved separately from other concentrate components contained in the other compartments. Then, in a second step RO water is fed into the second compartment which contains anhydrous citric acid as a concentrate component. The RO water dissolves the citric acid and passes from the second concentrate compartment into the third concentrate compartment, which contains calcium chloride as a concentrate component, by opening the piston valve due to the flow and/or the fluid pressure. Thereby, the calcium chloride is dissolved. Using this step sequence, undesired effects arising from degassing and/or precipitation of one or more of the concentrate components due to intermixing of the concentrate components and due to the dilution process can be avoided.

The method according to embodiments of the invention allows providing and/or storing different concentrate components in separate concentrate compartments before preparing the medical fluid. Further, preparation of the medical fluid may be performed in separate compartments of the concentrate container by individually diluting, dissolving and/or suspending different concentrate components of the medical fluid and combining them subsequently. Thereby, degradation and caking of the concentrate components due to mixing of the components before dilution by the diluent may be avoided. Further, by performing a suitable dilution sequence for the different concentrate components, degassing and precipitation of concentrate components during dilution can be reduced or avoided. Consequently, a complete dissolution of the concentrate components or concentrates, respectively, contained in the concentrate container can be achieved, in order to form the medical fluid.

According to embodiments of the method for preparing a medical fluid, during feeding the diluent a first diluent is fed into the first compartment and a second diluent is fed into the second compartment, the first diluents and the second diluent being different from each other. Thereby, different solvents can be used for different concentrates of concentrate components depending on the solubility thereof.

In the method of embodiments, feeding of the diluents may be performed via at least one diluent inlet and transferring of the diluted concentrate components may be performed via at least one medical fluid outlet, the at least one diluent inlet and the at least one medical fluid outlet being separate from each other.

While the foregoing is directed to examples and embodiments of the invention, other and further embodiments of the invention may be devised. Especially, mutually non-exclusive features of the examples and embodiments described above may be combined with each other.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A dry peritoneal dialysis (PD) concentrate system, comprising:
   a dry PD concentrate container including a first concentrate compartment and a second concentrate compartment, wherein the first concentrate compartment has a diluent inlet, wherein the second concentrate compartment has a medical fluid outlet, and wherein at least one of the first and second concentrate compartments contains a dry PD concentrate component;
   a first fluid container for collecting a prepared dialysis solution, the first fluid container being fluidly connected to a medical fluid removal line;
   a fluid transfer line fluidly connecting the medical fluid outlet of the concentrate container and the first fluid container; and
   a second fluid container for collecting a consumed dialysis solution connected to a consumed medical fluid line, wherein the first fluid container is located within the second fluid container.

2. The dry PD concentrate system of claim 1, wherein the first concentrate compartment and the second concentrate compartment are separated from each other by a barrier.

3. The dry PD concentrate system of claim 1, wherein the concentrate container includes a third concentrate compartment that is separated from the second concentrate compartment by a barrier.

4. The dry PD concentrate system of claim 1, wherein at least two different concentrate components are provided in different ones of the concentrate compartments.

5. The dry PD concentrate system of claim 1, wherein at least one of the first fluid container or the second fluid container is flexible and/or the concentrate container is rigid.

6. The dry PD concentrate system of claim 1, wherein the system is adapted to be a mobile system.

7. The dry PD concentrate system of claim 6, further comprising a transport device for enabling mobility of the mobile system.

8. The dry PD concentrate system of claim 1, wherein the system is adapted to be a modular system.

9. The dry PD concentrate system of claim 8, wherein at least two elements chosen from the concentrate container, the first fluid container, the second fluid container are modular components of the system.

10. The dry PD concentrate system of claim 1, wherein the first concentrate compartment contains a first dry PD concentrate component, and wherein the second concentrate compartment contains a second dry PD concentrate component.

11. The dry PD concentrate system of claim 10, wherein the first concentrate compartment and the second concentrate compartments are adapted to avoid mixing of the first dry PD concentrate component and the second dry PD concentrate component until a diluent is added via the diluent inlet.

12. A peritoneal dialysis (PD) system, comprising:
a PD cycler; and
a dry PD concentrate system connected to the PD cycler, the dry PD concentrate system comprising:
  a dry PD concentrate container including a first concentrate compartment and a second concentrate compartment, wherein the first concentrate compartment has a diluent inlet, wherein the second concentrate compartment has a medical fluid outlet, and wherein at least one of the first and second concentrate compartments contains a dry PD concentrate component;
  a first fluid container for collecting a prepared dialysis solution, the first fluid container being fluidly connected to a medical fluid removal line;
  a fluid transfer line fluidly connecting the medical fluid outlet of the concentrate container and the first fluid container; and
  a second fluid container for collecting a consumed dialysis solution connected to a consumed medical fluid line, wherein the first fluid container is located within the second fluid container.

13. The PD system of claim 12, wherein the first concentrate compartment and the second concentrate compartment are separated from each other by a barrier.

14. The PD system of claim 12, wherein the concentrate container includes a third concentrate compartment that is separated from the second concentrate compartment by a barrier.

15. The PD system of claim 12, wherein at least two different concentrate components are provided in different ones of the concentrate compartments.

16. The PD system of claim 12, wherein at least one of the first fluid container or the second fluid container is flexible and/or the concentrate container is rigid.

17. The PD system of claim 12, wherein the PD system is adapted to be a mobile system.

18. The PD system of claim 17, further comprising a transport device for enabling mobility of the mobile system.

19. The PD system of claim 12, wherein the PD system is adapted to be a modular system.

20. The PD system of claim 19, wherein at least two elements chosen from the concentrate container, the first fluid container, the second fluid container are modular components of the system.

21. The PD system of claim 12, wherein the first concentrate compartment contains a first dry PD concentrate component and wherein the second concentrate compartment contains a second dry PD concentrate component.

22. The PD system of claim 21, wherein the first concentrate compartment and the second concentrate compartments are adapted to avoid mixing of the first dry PD concentrate component and the second dry PD concentrate component until a diluent is added via the diluent inlet.

* * * * *

UNITED STATES PATENT AND TRADEMARK OFFICE
CERTIFICATE OF CORRECTION

| | | |
|---|---|---|
| PATENT NO. | : 10,076,599 B2 | Page 1 of 1 |
| APPLICATION NO. | : 15/091298 | |
| DATED | : September 18, 2018 | |
| INVENTOR(S) | : Thierry Eyrard, Philippe Laffay and Benoit Luaire | |

It is certified that error appears in the above-identified patent and that said Letters Patent is hereby corrected as shown below:

On the Title Page

Column 1, Inventors (72), Line 1, delete "Lyons (FR);" and insert --Lyon (FR);--.

Signed and Sealed this
Ninth Day of March, 2021

Drew Hirshfeld
*Performing the Functions and Duties of the
Under Secretary of Commerce for Intellectual Property and
Director of the United States Patent and Trademark Office*